United States Patent
Blankenship

(10) Patent No.: US 6,218,557 B1
(45) Date of Patent: Apr. 17, 2001

(54) SYNTHESIS OF TITANOCENES

(75) Inventor: Craig Blankenship, Longmont, CO (US)

(73) Assignee: Boulder Scientific Company, Mead, CO (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/117,090
(22) PCT Filed: Nov. 22, 1996
(86) PCT No.: PCT/US96/18666
§ 371 Date: Jul. 22, 1998
§ 102(e) Date: Jul. 22, 1998
(87) PCT Pub. No.: WO98/22476
PCT Pub. Date: May 28, 1998

(51) Int. Cl.$^7$ ............................... C07F 17/00; C07F 7/28
(52) U.S. Cl. ............................ 556/11; 556/53; 526/126; 526/160; 526/943; 502/103; 502/117
(58) Field of Search .................. 556/11, 53; 502/103, 502/17; 526/126, 160, 943

(56) References Cited

U.S. PATENT DOCUMENTS

| | | | |
|---|---|---|---|
| 5,350,723 | * | 9/1994 | Neithamer et al. ............... 502/104 |
| 5,504,224 | * | 4/1996 | Wilson ................................ 556/10 |
| 5,532,394 | * | 7/1996 | Rosen et al. ....................... 556/11 |
| 5,688,880 | * | 11/1997 | Spencer et al. .................. 526/127 |
| 5,866,704 | * | 2/1999 | Nickias et al. ..................... 556/11 |

OTHER PUBLICATIONS

Feld et al., The Organic Chemistry of Titanium, Washington D.C. (Butterworths) p. 154, 1965.*

Cotton et al., Advanced Inorganic Chemistry A Comprehensive Text, New York (John Wiley & Sons) p. 701, 1980.*

* cited by examiner

Primary Examiner—Porfirio Nazario-Gonzalez
(74) Attorney, Agent, or Firm—Edward S. Irons

(57) ABSTRACT

A method for the preparation of titanium-containing metallocene compounds, including constrained geometry titanium complexes, useful as olefin polymerization catalysts is disclosed. Pursuant to the invention, titanium tetrachloride is converted to titanium trichloride by reaction with a metal compound in a non-interfering solvent to produce a mixture useful directly for reaction with a deprotonated metallocene ligand. The titanocene compounds produced pursuant to the invention are free of trace amounts of aluminum which can adversely affect the polymerization reaction.

12 Claims, 1 Drawing Sheet

SYNTHESIS OF TITANOCENES

FIELD OF THE INVENTION

This invention relates to the synthesis of titanocenes including constrained geometry titanocene catalysts utilizing a unique titanium trichloride reagent.

BACKGROUND OF THE INVENTION

The evolution of metallocene-based catalysts for the polymerization of ethylene and higher α-olefins is reviewed in H. H. Brintzinger, et al., *Angew. Chem. Int. Ed. Engl.* 34: 1143–1170 (1995) and in P. C. Mohring, et al., *J. Organometal. Chem.* 479: 1–29 (1994). The applications of chiral metallocenes in organic synthesis are reviewed in R. L. Halterman, *Chem. Rev.* 92: 965–994 (1992). These reviews highlight the applications of state-of-the art metallocenes. Most often, these applications center on the use of titanium containing and other Group IV metallocenes.

The early preparations of Group IV metallocenes involved reactions of the metal tetrahalides, typically the tetrachlorides, with deprotonated ligands, such as sodium cyclopentadienide, to give the metallocenes in good yields. The metallocenes of current interest possess more complicated ligand structures, and their preparations are not as straightforward. For the preparation of these metallocenes, the use of titanium tetrachloride often results in low yields of the desired metallocenes. Titanium trichloride ($TiCl_3$) is often specified for use in place of titanium tetrachloride ($TiCl_4$); subsequent oxidation gives the desired metallocenes in greatly improved yields.

For some recent examples which specify the use of titanium trichloride, see L. A. Paquette, et al., *Organometallics* 14: 4865–4878 (1995); F. Zaegel, et al., *Organometallics* 14: 4576–4584 (1995); and M. E. Huttenloch, et al., *Organometallics* 11: 3600–3607 (1992). Halterman, supra, cites references which show the use of titanium trichloride in several metallocene preparations. The titanium trichloride so used is produced from commercial titanium tetrachloride. Titanium trichloride produced by hydrogen reduction of the tetrachloride is most often used in lab-scale preparations. For commercial-scale preparations, this is impractical due to cost and the presence of acidic impurities. These impurities require purification of the titanium trichloride, typically by preparation and isolation of an ether complex, usually the tetrahydrofuran complex.

Commercially-available titanium trichloride is produced by the reduction of the tetrachloride with alkyl aluminum compounds. The titanium trichloride so produced contains aluminum chloride, which is not removed. Typical analyses specify 76–79 weight percent of titanium trichloride with the remaining weight percent comprised mostly of aluminum chloride. The use of aluminum-reduced titanium trichloride in metallocene preparations often gives products which contain varying amounts of aluminum-containing impurities. Separation of these impurities from the product titanocenes is not straightforward in most cases, especially on a commercial scale. The presence of these impurities can have significant adverse effects during subsequent uses of the titanocenes, particularly in olefin polymerizations.

Accordingly, a need exists for a titanium trichloride reagent useful to produce titanocenes free of aluminum containing impurities.

DEFINITIONS

For the purposes of this invention, the following terms have the meaning stated:

Titanocene Compound—A compound comprised of titanium bonded to one or more cyclopentadienyl rings.

Titanocene Ligand—A chemical precursor which contains cyclopentadienyl or substituted cyclopentadienyl moieties (including indenyl, fluorenyl, etc.) used to prepare a titanocene compound.

Constrained Geometry Catalyst (CGC)—A catalyst in which the metal center is contained in a ring structure and covalently bonded to a cyclic group via a delocalized π-system and covalently bonded via a sigma-bond to another atom such as carbon, nitrogen, oxygen, etc. A small ring size induces constraint about the metal atom center. For titanium-containing CGC's, the incorporated titanium atom can be in a formal +4, +3, or +2 oxidation state. See EP application 90309496.9, WO 95/00526 and U.S. Pat. No. 5,470,996.

CpSA Ligand—(t-butylamino)(tetramethylcyclopentadienyl)dimethylsilane.

$(CpSA)^{2-}$—doubly-deprotonated CpSA ligand.

$(CpSA)^{2-}TiCl_2$—[(t-butylamido)(tetramethylcyclopentadienyl)dimethylsilane]titanium dichloride.

Substantially Stoichiometric Amount—An amount not less than 90% nor more that 110% of stoichiometric.

SUMMARY OF THE INVENTION

This invention includes a general method for producing titanium trichloride containing mixtures suitable for the preparation of titanium-containing metallocenes including constrained geometry Ti(IV), Ti(III) and Ti(II) complexes free of aluminum containing impurities.

The titanium trichloride containing mixtures are produced by the preferably stoichiometric (1:1) reaction of an organometallic compound, such as n-butyl lithium or n-butyl magnesium chloride, with titanium tetrachloride in a non-interfering solvent medium. These mixtures are used directly without isolation of the titanium trichloride in reactions with appropriate ligands to produce the desired titanocenes, including constrained geometry titanium complexes, in good yields. The resulting titanocene products are specifically free of aluminum-containing impurities.

DETAILED DESCRIPTION OF THE INVENTION

The invention is a method for producing a titanium-containing metallocene compound which comprises separately providing a first reaction mixture containing titanium trichloride and a second reaction mixture containing a magnesium or alkali metal or alkaline earth metal salt of a metallocene compound ligand. The first and second mixtures are combined for reaction to produce an intermediate from which an aluminum-free titanocene useful as an olefin polymerization catalyst may be synthesized.

The first reaction mixture is produced by reacting $TiCl_4$ with an alkali metal compound having the formula $R_X$—M or a Grignard reagent having the formula RMgX. In each formula, R is a straight or branched chain aliphatic hydrocarbon group, preferably an alkyl group, having 2 to 10 carbon atoms. R may also be an alkaline earth metal such as calcium, barium or strontium. X is the value of M. In the formula $R_X$—M, M is an alkali metal such as sodium, potassium or lithium. In the formula RMgX, X is a halogen, preferably chlorine. n-butyl lithium or n-butyl magnesium chloride are preferred. The reactants are combined in substantially stoichiometric amounts in a non-interfering, preferably hydrocarbon, medium.

Useful hydrocarbon media include aliphatic or aromatic hydrocarbons, such as hexane, heptane, cyclohexane, benzene, toluene and xylene. Toluene is preferred for the specific examples shown here. Useful ether and polyether solvents include tetrahydrofuran, diethyl ether, ethylene glycol dimethyl ether, and dioxane. Mixtures of any hydrocarbon and ether solvents are useful for the reaction.

The reaction is preferably accomplished under dry, oxygen-free conditions. The temperature at which the reaction is conveniently conducted is −20° C. or 120° C., with the optimum temperature range being 30–40° C.

The second reaction mixture is separately provided by deprotonating the desired metallocene ligand with the appropriate base by known methods. See, generally, Paquette, et al., supra; Zaegel, et al., supra; and Halterman, supra.

The first reaction mixture, which includes the medium or solvent, titanium trichloride and a metal halide such a LiCl or $MCl_2$, is added directly without isolation of the titanium trichloride to the second deprotonated ligand reaction mixture to produce a first titanocene.

Step (1)—Aluminum-Free $TiCl_3$

Figure 1:
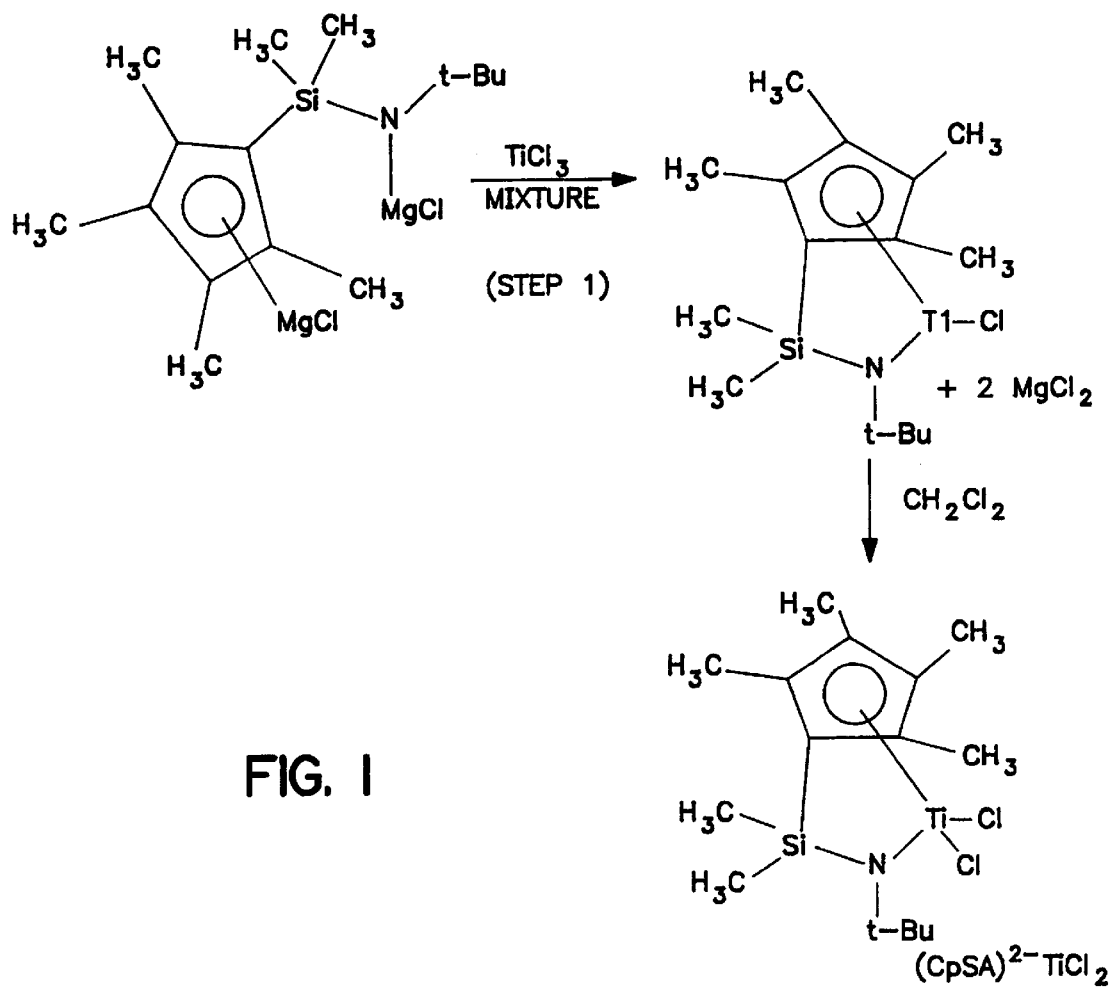
FIG. 1 is a generalized depiction of steps (1), (2), and (3) as comprised by one embodiment of the invention for preparation of a Ti(IV) complex constrained geometry catalyst.

Step (1) of FIG. 1 illustrates the reaction of $TiCl_4$ in substantially stoichiometric amount with n-butyl lithium or n-butyl magnesium chloride to produce $TiCl_3$ and lithium or magnesium chloride in a hydrocarbon or ether medium, or mixed hydrocarbon and ether medium.

Step (2)—Deprotonation Of a Metallocene Compound Ligand

Step (2) of FIG. 1 illustrates the double deprotonation of the metallocene compound ligand (t-butylamino) (tetramethylcyclopentadienyl)dimethylsilane (CpSA ligand) with an organometallic deprotonating agent, preferably an organolithium or an organomagnesium compound (Grignard reagent), in a hydrocarbon medium, preferably toluene.

The solvent medium and the organometallic compound may be the same as or different from the solvent medium and the organometallic compound used in Step (1). The concentration of the CpSA ligand in the solvent is appropriately 0.05 to 1.5 M, preferably 0.45 to 0.6 M.

Any Grignard reagent may be used to deprotonate the metallocene compound ligand, e.g., CpSA. Useful Grignard reagents have the formula RMgX as defined above. Isopropyl magnesium chloride is preferred. A practical range of Grignard concentration in the solvent is 0.5 to 3.0 M, preferably 1.9 to 2.3 M. For CpSA, the temperature is controlled to be 45–50° C. at the end of the Grignard feed, and then heated to 85–90° C. for the prescribed time.

The Step (2) reaction mixture is preferably used directly in Step (3) as the toluene solution present in the reaction vessel in which it is produced.

Step (3)—Reaction of $TiCl_3$ With Deprotonated Ligands—Production of $(CpSA)^{2-}$—$TiCl_2$ Step (3) of FIG. 1 illustrates one method for reacting the titanium trichloride containing reaction mixture of Step (1) with the $(CpSA)^{2-}$-containing second reaction mixture of Step (2) to produce [(t-butylamido) (tetramethylcyclopentadienyl) dimethylsilane]titanium dichloride, $(CpSA)^{2-}TiCl_2$.

In this embodiment of the invention, the agitated Step (1) reaction mixture is transferred directly into the reactor containing agitated Step (2) reaction mixture. Preferably, the vessel which contained the Step (1) mixture is rinsed with toluene which is then charged to the Step (3) reactor. The exothermic reaction mixture becomes reddish brown in color. A temperature rise of about 15° C. is usually observed.

A chloride-containing oxidizing agent, such as dichloromethane or silver chloride, is then charged to the reaction vessel utilized in Step (3). The resulting reaction mixture is agitated for a time appropriate, usually about two hours, for the Step (3) reaction to occur.

Solvents are removed under reduced pressure, i.e., 60–80 mm Hg, to about one-half of the starting volume. Hydrocarbon solvent, e.g., toluene, is added back, Celite® filter aid is added, and the mixture is filtered. Solvents are distilled to concentrate the product.

The solid titanocene can be isolated from this mixture by methods dependent upon the actual compound being produced. For the $(CpSA)^{2-}TiCl_2$ example shown in FIG. 1, the solid product was collected in 75–80% yield as described in Example 6. Additional material of lower purity can be isolated upon further manipulation of the mother liquors. Alternatively, the product solution obtained after removal of the magnesium salts can be used directly to produce other metallocenes described in Example 6.

EXEMPLIFICATION OF THE INVENTION

Preparative Procedures For Titanium Trichloride Reactant Mixtures and Resulting Metallocenes The general procedure for the preparation of titanium trichloride-containing mixtures by the reaction of titanium tetrachloride and an organometallic compound under an inert atmosphere is first described, followed by three specific examples. The reaction apparatus consisted of a 500-mL 3-neck flask equipped with a mechanical stirrer. On one side-neck was placed a Claisen adapter with a reflux condenser and a thermometer inserted into the reaction mixture. This apparatus was previously dried and then purged with nitrogen after assembly. The solvent was added via the other side-neck of the reaction flask, which was then capped with a rubber septum. $TiCl_4$ (ca. 25 mL, 42–44 g. 0.22–0.23 mol) was transferred from a weighed bottle to the reaction flask using a syringe. The rubber septum was replaced with a dried, nitrogen-purged addition funnel. The THF and/or the organometallic compound was transferred to the addition funnel and then added to the $TiCl_4$/solvent reaction mixture at the desired temperature.

EXAMPLE 1

A solution of n-butyllithium (BuLi) in hexanes (156 mL of a 1.60 M solution, 0.250 mol of BuLi) was added to $TiCl_4$ (43.0 g, 0.227 mol) in 300 mL of toluene over 30 min. The initial temperature of the reaction mixture was 10° C., the temperature increased to 40° C. during the addition, and was then maintained at 35–40° C. using external cooling. After the addition of the BuLi, the reaction mixture was stirred at 35–40° C. for 1 hour. After cooling to room temperature, the addition funnel, condenser, and Claisen adapter were removed while maintaining an inert atmosphere of nitrogen over the $TiCl_3$ product mixture. The resulting $TiCl_3$ containing mixture was used directly in reactions with deprotonated metallocene ligands.

EXAMPLE 2

THF (100 mL) was added to a solution of $TiCl_4$ (43.4 g, 0.229 mol) in 200 mL of toluene over 30 minutes at 0–15° C. Then BuLi in hexanes (156 mL of a 1.60 M solution, 0.250 mol) was added over 40 min at 5–10° C. The resulting mixture was heated to 35–40° C. and stirred for 1 hour. After cooling, the resulting $TiCl_3$ slurry was used directly in reactions with deprotonated ligands.

EXAMPLE 3

THF (75 mL) was added to a solution of $TiCl_4$ (42.0 g, 0.221 mol) in 150 mL of toluene over 20 min at 0–15° C. Then a solution of butylmagnesium chloride (BuMgCl) in THF (115 mL of a 2.10M solution, 0.242 mol of BuMgCl) was added over 30 min. The initial temperature of the reaction mixture was 0° C.; the temperature increased to 40° C. during the addition and was then maintained at 35–40° C. using external cooling. After the BuMgCl addition, the reaction mixture was stirred for 1 hour at 35–40° C. The resulting $TiCl_3$ product slurry was used directly in reactions with deprotonated ligands.

EXAMPLE 4

The Deprotonation of CpSA Ligand With i-Propylmagnesium Chloride

The reaction apparatus consisted of a 2000-mL 3-neck flask equipped with a mechanical stirrer; on one side-neck was placed a Claisen adapter with a Vigereaux column and distillation head for solvent distillation. A thermometer was inserted into the reaction flask through the Claisen adapter. The glass apparatus was previously dried and purged with nitrogen after assembly. Toluene (425 mL) and CpSA ligand (55.0 g, 0.219 mol) were added to the reaction flask. The temperature of the reaction mixture was adjusted to 45–50° C. A solution of i-propylmagnesium chloride (i-PrMgCl) in ether (205 mL of a 2.30 M solution, 0.472 mol of i-PrMgCl) was added over 1 hour using an addition funnel. After the i-PrMgCl addition, the reaction mixture was gradually heated to 85–90° C. over 2 hours and stirred at this temperature for an additional 2 hours. The $(CpSA)^{2-}(MgCl)_2$ formed a gummy solid at this stage. The heating is removed and the temperature of the reaction mixture cooled to 60–65° C. At this temperature, THF (150 mL) was added dropwise over 15 min, which dissolved the solid $(CpSA)^{2-}(MgCl)_2$. The reaction mixture is then cooled to room temperature. The distillation head, Vigereaux column, and addition funnel are then removed from the reaction apparatus while maintaining an inert atmosphere of nitrogen over the product mixture. This $(CpSA)^{2-}(MgCl)_2$ solution was then used directly in a reaction with a $TiCl_3$ slurry prepared previously.

EXAMPLE 5

The Deprotonation of CpSA Ligand with n-Butyllithium

The reaction apparatus consisted of a 2000-mL 3-neck flask equipped with a mechanical stirrer; on one side-neck was placed a Claisen adapter with a reflux condenser and a thermometer inserted into the reaction flask. The glass apparatus was previously dried and purged with nitrogen after assembly. Ether (300 mL) and CpSA ligand (62.9 g, 0.250 mol) were added to the reaction flask. The reaction mixture was cooled to −20° C. A solution of BuLi in hexanes (305 mL of a 0.170 M solution, 0.518 mol of BuLi) was added over 1.5 hours; the temperature was maintained at −20 to −15° C. during this addition. The reaction mixture was then warmed to 0–5° C. over 1.5 hours and stirred at this temperature for 3 hours. The resulting $(CpSA)^{2-}Li_2$ slurry, which consisted of a white solid with a pale yellow supernatant, was used directly in a reaction with a $TiCl_3$ slurry prepared as described in Examples 1 to 3.

EXAMPLE 6

The Preparation of $(CpSA)^{2-}TiCl_2$

The $TiCl_3$ containing mixture from Example 1 above was transferred under nitrogen pressure via a wide-bore cannula to the $(CpSA)^{2-}(MgCl)_2$ solution from Example 4 above over 2–3 min. Toluene (100 mL) was added to the $TiCl_3$ flask which contained some residual $TiCl_3$, and this wash was quickly transferred to the reaction flask. The initial temperature of the reaction mixture was 22° C.; the temperature increased to 35° C. during the $TiCl_3$ addition. The reaction mixture was stirred for 15 min at 35° C., at which time dichloromethane (13.5 g) was added over 1 min; the temperature increased to 38° C. The resulting red-brown mixture was stirred for 2 hours with gradual cooling to 25° C. Solvents were removed by simple distillation under reduced pressure (60–80 mm Hg) to a final volume of ca. 600 mL; the temperature ranged from 30 to 60° C. during this distillation. After cooling to 20° C. and pressurizing with nitrogen, toluene (400 mL) was added to the product mixture. Magnesium salts were removed from this mixture by pressure filtration under nitrogen using Celite® filter-aid. The reaction flask and filter cake were washed with two 200-mL portions of fresh toluene. The red-brown filtrate was concentrated by simple distillation under reduced pressure as before to a volume of 400 mL. This toluene solution is again filtered under nitrogen pressure to remove residual magnesium salts. The filtrate is concentrated again to a volume of 200 mL by simple distillation under reduced pressure. Heptanes (400 mL) were added over 30 min with stirring at 20–25° C. A first crop of orange, crystalline $(CpSA)^{2-}TiCl_2$ is collected by filtration under nitrogen, washing with heptanes, to give 61.1 g of product in 76% yield. A second crop was obtained by concentration of the mother liquors to ca. 100 mL and dilution with heptanes.

Alternatively, the product solution in toluene obtained after removal of the magnesium salts was used directly to prepare other metallocenes. For example, the toluene solution of $(CpSA)^{2-}TiCl_2$ was treated with 2 equivalents of methylmagnesium chloride (THF solution) to give $(CpSA)^{2-}Ti(CH_3)_2$ in 70–75% overall yield.

What is claimed is:

1. In a process for producing a constrained geometry titanocene catalyst wherein a titanium trichloride reagent is reacted with a constrained geometry titanocene catalyst, the improvement which comprises:
   (i) utilizing as said titanium trichloride reagent a mixture produced by reacting titanium tetrachloride with a compound having the formula R—M, in which R is a straight or branched chain alkyl group having 2 to 8 carbon atoms and M is an alkali metal, or the formula RMgX, in which X is a halogen in substantially stoichiometric amount in a non-interfering solvent wherein a reaction mixture containing titanium trichloride, said solvent and a MCl or $MgCl_2$ is produced; and
   (ii) reacting said step (i) reaction mixture directly with said titanocene ligand to produce a titanocene.

2. The process of claim 1 in which said titanium trichloride and said ligand are reacted at a temperature in the range of −20 to 120° C.

3. The process of claim 1 in which said compound RM is added to titanium tetrachloride at an initial temperature range of 10–20° C., after which the reaction mixture is heated to 34–40° C. for about one hour.

4. The process of claim 1 in which an non-interfering solvent is an ether.

5. The process of claim 4 in which the ether solvent is a cyclic ether or a polyether.

6. In a process for producing a constrained geometry titanocene catalyst wherein a titanium trichloride reagent is reacted with a constrained geometry titanocene catalyst ligand, the improvement which comprises:

(i) utilizing as said titanium trichloride reagent a mixture produced by reacting titanium tetrachloride with a compound having the formula R-M, in which R is a straight or branched chain alkyl group having 2 to 8 carbon atoms and M is an alkali metal, or the formula RMgX, in which X is a halogen in substantially stoichiometric amount in a non-interfering solvent wherein said non-interfering solvent is a hydrocarbon; and (ii) reacting said step (i) reaction mixture directly with said said constrained geometry titanocene catalyst ligand to produce a titanocene.

7. The claim 6 process wherein said hydrocarbon solvent is a hexane, heptane, a benzene, a toluene, a xylene, or a mixture thereof.

8. The claim 6 process wherein said non-interfering solvent is dimethyl ether, diethyl ether or dibutyl ether.

9. In a process for producing a titanocene wherein a titanium trichloride reagent is reacted with a titanocene ligand, the improvement which comprises:

(i) utilizing as said titanium trichloride reactant a mixture produced by reacting titanium tetrachloride with a compound having the formula R—M, in which R is a straight or branched chain alkyl group having 2 to 8 carbon atoms and M is an alkali metal, or the formula RMgX, in which X is a halogen in substantially stoichiometric amount in a non-interfering liquid medium wherein a reaction mixture containing titanium trichloride, said solvent and MCl or $MgCl_2$ is produced;

(ii) reacting, said step (i) reaction mixture with a deprotonated titanocene ligand to produce a second reaction mixture including said liquid medium, and a titanocene corresponding to said titanocene ligand; and (iii) optionally isolating said titanocene of step (ii) from said step (ii) second reaction mixture.

10. In a process for producing a titanocene wherein a titanium trichloride reactant is reacted with titanocene ligand, the improvement which comprises:

(i) utilizing as said titanium trichloride reactant a mixture produced by reacting titanium tetrachloride with a compound having the formula R—M, in which R is a straight or branched chain alkyl group having 2 to 10 carbon atoms and M is an alkali metal, or the formula RMgX, in which X is a halogen in substantially stoichiometric amount in a non-interfering solvent wherein a reaction mixture containing titanium trichloride, said solvent and MCl or $MgCl_2$ is produced;

(ii) reacting said step (i) mixture with a deprotonated titanocene ligand to produce a reaction mixture including said solvent, and a titanocene corresponding to said titanocene ligand and MCl or $MgCl_2$;

(iii) separating said MCl or $MgCl_2$ from said step (ii) reaction mixture; and thereafter (iv) utilizing said step (ii) reaction mixture to prepare another titanocene.

11. A method for producing a constrained geometry titanocene catalyst which comprises:

(i) reacting n-butyl lithium or isobutyl lithium with titanium tetrachloride in substantially stoichiometric amount in a non-interfering hydrocarbon medium to produce a first reaction mixture containing titanium trichloride and lithium chloride; and (ii) combining said first reaction mixture with a titanocene ligand in a non-interfering medium for reaction to produce a titanocene corresponding to said ligand.

12. The claim 11 method in which said titanocene corresponding to said ligand produced in step (ii) is $(CpSA)^{2-}TiCl_2$ ([(t-butylamido) (tetramethylcyclopentadienyl) dimethylsilane]titanium dichloride).

* * * * *

UNITED STATES PATENT AND TRADEMARK OFFICE
CERTIFICATE OF CORRECTION

PATENT NO. : 6,218,557 B1  
DATED : April 17, 2001  
INVENTOR(S) : Craig Blankenship Page 1 of 1

It is certified that error appears in the above-identified patent and that said Letters Patent is hereby corrected as shown below:

Title page,
OTHER PUBLICATIONS, -- Mach, et al., Journal of Organometallic Chemistry, Vol. 33, pages 205-215 (1987) --

Column 6, claim 1,
Line 51, after the word "catalyst", insert -- ligand --

Column 7, claim 6,
Line 23, delete second "said"

Signed and Sealed this

Second Day of April, 2002

Attest:

*Attesting Officer*

JAMES E. ROGAN  
*Director of the United States Patent and Trademark Office*